United States Patent
Ko

(10) Patent No.: US 11,123,498 B2
(45) Date of Patent: Sep. 21, 2021

(54) TREATMENT DEVICE AND METHOD FOR CONTROLLING SAME

(71) Applicant: LUTRONIC CORPORATION, Goyang (KR)

(72) Inventor: Kwang Chon Ko, Paju (KR)

(73) Assignee: LUTRONIC CORPORATION, Goyang (KR)

( * ) Notice: Subject to any disclaimer, the term of this patent is extended or adjusted under 35 U.S.C. 154(b) by 202 days.

(21) Appl. No.: 16/066,927

(22) PCT Filed: Nov. 17, 2016

(86) PCT No.: PCT/KR2016/013239
§ 371 (c)(1),
(2) Date: Jun. 28, 2018

(87) PCT Pub. No.: WO2018/092935
PCT Pub. Date: May 24, 2018

(65) Prior Publication Data
US 2018/0369505 A1     Dec. 27, 2018

(51) Int. Cl.
*A61M 5/46* (2006.01)
*A61M 37/00* (2006.01)
(Continued)

(52) U.S. Cl.
CPC ........... *A61M 5/46* (2013.01); *A61B 18/1402* (2013.01); *A61B 18/148* (2013.01); *A61M 5/32* (2013.01);
(Continued)

(58) Field of Classification Search
CPC ........ A61B 2090/062; A61B 2090/065; A61B 17/3472; A61M 5/46; A61M 5/32;
(Continued)

(56) References Cited

U.S. PATENT DOCUMENTS

| 2008/0058706 A1* | 3/2008 | Zhang | A61N 1/327 604/21 |
| 2014/0046261 A1* | 2/2014 | Newman | A61B 5/062 604/158 |

(Continued)

FOREIGN PATENT DOCUMENTS

| KR | 10-0896797 B1 | 5/2009 |
| KR | 10-2011-0000790 A | 1/2011 |

(Continued)

OTHER PUBLICATIONS

International Search Report for PCT/KR2016/013239 filed on Nov. 17, 2016.

(Continued)

*Primary Examiner* — Kevin C Sirmons
*Assistant Examiner* — Antarius S Daniel

(57) ABSTRACT

The present invention relates to a treatment device and a method for controlling the same, and provides a treatment device comprising: an insertion unit formed to be insertable in tissue after penetrating through a surface of the tissue; a displacement measuring unit for measuring displacement of the surface of the tissue, caused by an insertion of the insertion unit; and a control unit for controlling an insertion motion of the insertion unit on the basis of the displacement measured by the displacement measuring unit. According to the present invention, the device allows medical treatment in a state in which the insertion unit has been inserted to reach a precise position of a target, so as to improve an effect of medical treatment.

20 Claims, 15 Drawing Sheets

(51) Int. Cl.
    *A61M 5/32*     (2006.01)
    *A61B 18/14*     (2006.01)
    *A61N 1/40*     (2006.01)
    *A61B 90/00*     (2016.01)
    *A61B 18/00*     (2006.01)

(52) U.S. Cl.
CPC ........ *A61M 37/00* (2013.01); *A61M 37/0015* (2013.01); *A61B 18/1477* (2013.01); *A61B 2018/00452* (2013.01); *A61B 2018/00904* (2013.01); *A61B 2018/00928* (2013.01); *A61B 2018/00958* (2013.01); *A61B 2018/143* (2013.01); *A61B 2018/1475* (2013.01); *A61B 2018/1495* (2013.01); *A61B 2090/062* (2016.02); *A61B 2090/065* (2016.02); *A61B 2090/08021* (2016.02); *A61M 2037/0023* (2013.01); *A61M 2205/3306* (2013.01); *A61M 2205/3317* (2013.01); *A61M 2205/3375* (2013.01); *A61N 1/40* (2013.01)

(58) Field of Classification Search
CPC .............. A61M 37/00; A61M 37/0015; A61M 2205/3317; A61M 2037/0023; A61M 2205/3306; A61M 2037/0007
See application file for complete search history.

(56) References Cited

U.S. PATENT DOCUMENTS

2014/0194789 A1* 7/2014 Ko .................... A61N 1/06
                                                       601/18
2015/0209527 A1* 7/2015 Kang .................... A61M 5/46
                                                     604/506
2017/0290995 A1* 10/2017 Raylman ................ A61M 5/20

FOREIGN PATENT DOCUMENTS

| KR | 10-2011-0033610 A | 3/2011 |
| KR | 10-2013-0137409 A | 12/2013 |
| KR | 10-2016-0099332 A | 8/2016 |
| KR | 10-2016-0112733 A | 9/2016 |

\* cited by examiner

TREATMENT DEVICE AND METHOD FOR CONTROLLING SAME

CROSS-REFERENCE TO RELATED APPLICATIONS

The present specification is a U.S. National Stage of International Patent Application No. PCT/KR2016/013239 filed Nov. 17, 2016, the entire contents of which are incorporated herein by reference.

TECHNICAL FIELD

The present invention relates to a treatment apparatus and a method of controlling the same and, more particularly, to a treatment apparatus inserted into a tissue of the human body to perform treatment in an invasive manner and a method of controlling the same.

BACKGROUND ART

A method of treating a tissue may be divided into a method of treating a tissue outside the tissue and an invasive treatment method of treating a tissue by inserting some of or the entire treatment apparatus into the tissue. The invasive treatment method basically uses a treatment apparatus having a thin-necked insertion unit, such as a needle or a catheter. Treatment is performed after the treatment apparatus is inserted up to a target location within a tissue.

The invasive treatment method includes various treatment behaviors, such as delivering a treating substance to the inside of a tissue, performing surgical treatment through a mechanical operation in the state in which a specific tissue within a tissue is adjacent, or delivering energy to a target location within a tissue. The treatment method has been disclosed in Korean Patent Application Publication No. 10-2011-0000790, and is applied in various methods.

In general, in the invasive treatment method, in a process of inserting an insertion unit into a tissue, displacement may occur as a tissue surface is pressurized. Furthermore, as the diameter of the insertion unit is reduced for minimum invasion, the bending of the insertion unit may occur in the insertion process. Accordingly, the insertion unit is not inserted up to a desired target location. In this case, treatment sensitive to a depth in which the treatment is performed, such as skin treatment, may have a problem in that a treatment effect is low or another tissue is damaged.

DISCLOSURE

Technical Problem

An object of the present invention is to provide a treatment apparatus in which an insertion unit can be inserted up to a target location although displacement occurs in a tissue surface in a process of inserting the insertion unit into the tissue and a method of controlling the same.

Technical Solution

In order to accomplish the object, the present invention provides a treatment apparatus, including an insertion unit formed in such a way as to be inserted into a tissue through a tissue surface, a displacement measurement unit measuring displacement of the tissue surface occurring due to an insertion of the insertion unit, and a controller controlling the insertion operation of the insertion unit based on the displacement measured by the displacement measurement unit.

The controller controls the insertion unit so that the insertion unit is additionally inserted as much as a size corresponding to the displacement occurred in the tissue surface so that the end of the insertion unit reaches up to a target location within the tissue. Specifically, the controller may control the insertion unit based on the depth of the target location so that the insertion unit is advanced and inserted as much as a first length, and may control the insertion unit so that the insertion unit is inserted as much as a second length in order to compensate for a depth into which the insertion unit has not been inserted due to the displacement of the tissue surface.

In this case, the second length may have the same size as the displacement measured by the displacement measurement unit. Or, the second length may be a numerical value calculated using the size of the displacement measured by the displacement measurement unit as a variable.

The displacement measurement unit measures the displacement of the tissue surface before the insertion unit pressurizes the tissue surface and after the insertion unit is inserted through the tissue surface.

The displacement measurement unit may use a sensor using light.

Alternatively, the displacement measurement unit may use a movable member moved as displacement occurs in the tissue surface and a sensing member measuring the amount of movement of the movable member. Specifically, the movable member includes a magnetic body, and the sensing member may be configured to sense the amount of movement of the movable member based on a change in the magnetic field generated when the movable member moves.

For example, the insertion unit may be provided in a tip module detachably positioned in a handpiece or a main body. The movable member may be provided to penetrate the tip module and positioned to be movable in the progress direction of the insertion unit. Furthermore, the sensing member may be disposed close to a portion which belongs to the handpiece or the main body and where the tip module is positioned.

In this case, the insertion unit may include a plurality of micro needles.

For example, the insertion unit may include an energy transfer member transferring energy to a target location in the state in which the insertion unit has been inserted into the tissue.

For another example, the insertion unit may include a substance transfer member transferring a treatment substance to a target location in the state in which the insertion unit has been inserted into the tissue.

Meanwhile, the present invention may provide a treatment apparatus, including a handpiece, an energy transfer unit formed in such a way as to pop in and out to and from one side of the handpiece and inserted into a tissue to transfer energy to a target location, a displacement measurement unit measuring displacement of the tissue surface occurring due to the insertion of the energy transfer unit, and a controller controlling the insertion operation of the energy transfer unit based on the displacement measured by the displacement measurement unit.

Furthermore, the present invention may provide a method of controlling a treatment apparatus, including the steps of positioning an insertion unit on a tissue surface, inserting the insertion unit into the tissue through the tissue surface by pressurizing the insertion unit, measuring displacement of the tissue surface occurring due to the insertion of the insertion unit, and controlling the insertion operation of the insertion unit based on the measured displacement.

The step of inserting the insertion unit into the tissue may include inserting the insertion unit by a first length based on the depth of the target location. The step of controlling the insertion operation of the insertion unit may include additionally inserting the insertion unit by a second length based on the size of the displacement of the tissue surface.

The step of controlling the insertion operation of the insertion unit may include the steps of calculating a compensation depth by taking into consideration the displacement of the tissue surface and additionally inserting the insertion unit as much as the calculated compensation depth.

Advantageous Effects

In accordance with the present invention, there is an advantage in that a treatment effect can be improved because treatment can be performed in the state in which the insertion unit has been inserted up to an accurate target location. Furthermore, a problem, such as damage to a neighboring tissue occurring because treatment is performed in the state in which the insertion unit has not been sufficiently inserted up to a target location, can be prevented.

MODE FOR INVENTION

Hereinafter, a treatment apparatus according to embodiments of the present invention are described in detail with reference to the drawings. In the following description, the location relations between elements are described in principle based on the drawings. Furthermore, the drawings may be enlarged and shown in order to simplify the structure of the invention for convenience of description or if necessary. Accordingly, the present invention is not limited thereto, and various devices may be added, changed or omitted.

Hereinafter, a "treatment apparatus" includes all apparatuses for treating mammals including people. The treatment apparatus may include may include various treatment apparatuses used to improve a lesion or the state of a tissue. For example, the treatment apparatus includes an apparatus transferring treating substances, such as medicines, anesthetic, and stem cells, an operation apparatus for surgically treating a specific tissue, and various treatment apparatuses transferring RF energy.

Hereinafter, a "tissue" means a set of cells forming various body organs of an animal including people, and includes various tissues forming various organs within the body, including a skin tissue.

Hereinafter, an "insertion unit" means an element that belongs to a treatment apparatus and that is inserted into a tissue. The insertion unit has a lengthy structure having a sharp and thin end, such as a needle, micro needle or a catheter, and includes various structures inserted into a tissue through a surface of the tissue.

Hereinafter, a treatment apparatus according to an embodiment of the present invention is described with reference to FIGS. 1 to 3.

Figure 1:
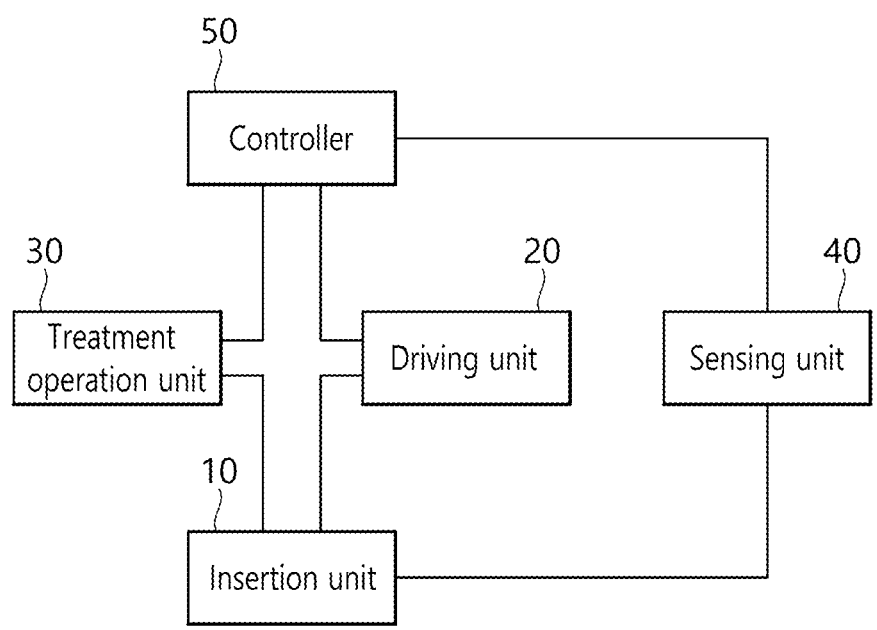
FIG. 1 is a block diagram showing the configuration of a treatment apparatus according to a first embodiment of the present invention.

FIG. 1 is a block diagram showing the configuration of a treatment apparatus according to a first embodiment of the present invention. As shown in FIG. 1, the treatment apparatus according to the present invention includes an insertion unit 10 formed in such a way as to be inserted into a tissue, a driving unit 20 moving the insertion unit, a treatment operation unit 30 for performing treatment on a tissue through the insertion unit, a sensing unit 40 for sensing displacement of a tissue surface, and a controller 50 controlling the operations of various elements, including the driving unit and the treatment unit.

The insertion unit 10 is an element inserted up to a tissue through a tissue surface as described above. The insertion unit 10 has a lengthy structure having a sharp end and a small diameter so that it can be easily inserted into a tissue. In the present embodiment, the insertion unit 10 includes a plurality of needles, but may have various structures, such as a singular needle structure or catheter. The insertion unit 10 further includes an element necessary for the execution of treatment depending on a treatment method of the treatment apparatus. For example, in the case of a treatment apparatus performing treatment using a method of transferring a treatment substance, the insertion unit may include a channel for injecting a treatment substance therein. Alternatively, in the case of a treatment apparatus performing treatment using a method of transferring RF energy to a tissue, the insertion unit may include an electrode for transferring RF energy. The insertion unit 10 is positioned in a handpiece, and may be configured to be advanced and retracted from and to the end of the handpiece and to be inserted into a tissue.

The driving unit 20 is an element that linearly moves the insertion unit 10 so that the insertion unit advances and retracts. The insertion unit 10 performs an operation of being inserted into a tissue or drawn out from a tissue by the driving of the driving unit 20. For example, the driving unit 20 may be configured using an actuator or may be configured using various driving members.

The treatment operation unit 30 is an element operating for the execution of treatment. The location where treatment is actually performed is the end of the insertion unit 10 positioned within a tissue. The treatment operation unit 30 is an element supporting a treatment operation performed at the end of the insertion unit. For example, the treatment operation unit may have a pump or valve for transferring a treatment substance from a treatment substance accommodation unit (not shown) to the end of the insertion unit. For another example, the treatment operation unit may be an RF generator for supplying RF energy to the end of the insertion unit. In addition, the treatment operation unit may have various elements depending on a treatment method of the treatment apparatus.

The controller 50 controls the operations of various elements of the treatment apparatus, including the driving unit 20 and the treatment operation unit 30. The controller 50 may perform treatment by driving the elements based on a user's control or a preset mode. The controller may further include a separate database or processor. Accordingly, when a variety of types of information necessary for control is transmitted to the controller, the controller may derive a proper control signal using previously stored data or a calculation method based on such information.

The sensing unit 40 is an element for sensing major parameters while the treatment apparatus operates. The sensing unit 40 of the present embodiment measures displacement of a tissue surface occurring as the insertion unit 10 is inserted into the tissue. Furthermore, a value measured by the sensing unit 40 is transferred to the controller 50. The controller 50 additionally controls the insertion depth of the insertion unit 10 based on the value.

Hereinafter, displacement occurring when the insertion unit is inserted is described in detail with reference to FIG. 2. FIG. 2 is a schematic diagram showing an example of a treatment step by the treatment apparatus of FIG. 1, and shows a process of inserting the insertion unit into a target location at a depth D into a tissue and performing treatment.

Figure 2A:
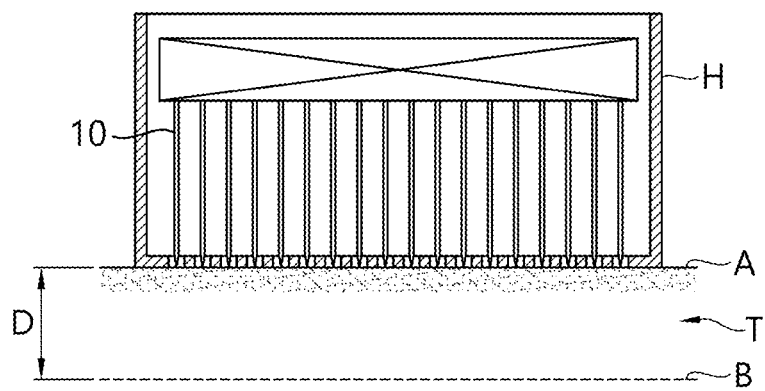
FIGS. 2a to 2d are schematic diagrams showing an example of a treatment step by the treatment apparatus of FIG. 1.
Figure 3:
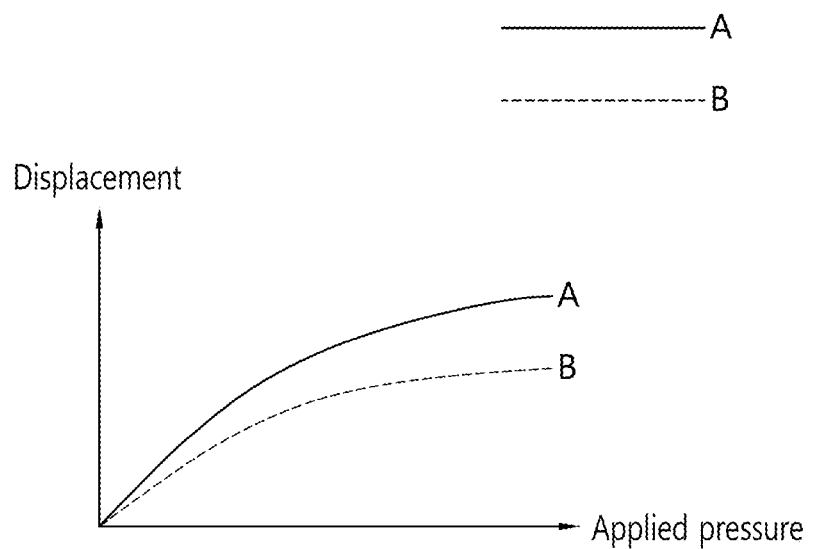
FIG. 3 is a graph showing the displacement characteristics of some tissues according to applied pressure.

FIG. 2a shows the state in which a handpiece H has been positioned on a surface of a tissue T. This step may be the state in which the driving unit has never been driven, and may be the state in which the driving unit has started to operate, but the end of the insertion unit has not come into contact with a tissue surface. As described above, FIG. 2a shows the state in which the insertion unit 10 has not pressurized a surface A of the tissue. Accordingly, separate displacement does not occur in the tissue surface, and separate displacement does not occur at a target location.

Figure 2B:
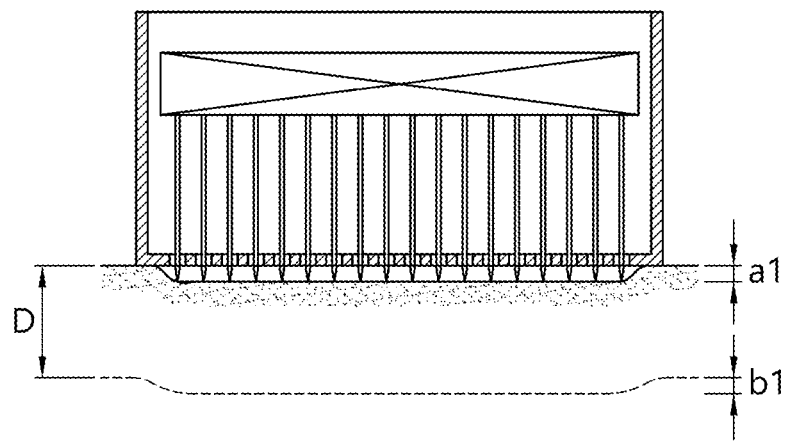

FIG. 2b shows the state in which the driving unit 20 operates and thus the end of the insertion unit 10 has pressurized the surface of the tissue. At the early stage of the insertion operation of the insertion unit 10, the surface of the tissue is pressurized in the state in which it has not been penetrated by the insertion unit. Accordingly, the surface A of the tissue experiences displacement of a1 in the inward direction of the tissue. The tissue has a structure in which cells, etc. have been organized with high density. Accordingly, when displacement occurs on the surface A of the tissue, a target location B also experiences displacement of b1 in the inward direction of the tissue.

Figure 2C:
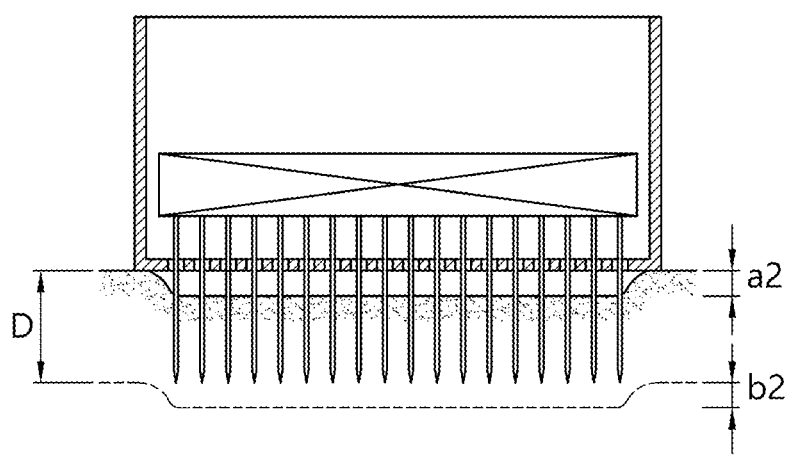

FIG. 2c shows the state in which the insertion unit 10 has been inserted into the tissue by advancing the insertion unit by a first length. In this case, the first length may be a length corresponding to D (depth with respect to a surface before the tissue surface is pressurized by the insertion unit), that is, the depth of the target location before the insertion unit is inserted into the tissue.

As shown in FIG. 2c, in this state, the surface of the tissue experiences displacement of a2 in the inward direction of the tissue, and the target location also experiences displacement of b2 in the inward direction of the tissue. The reason for this is that while the insertion unit 10 is inserted, a force acts in the direction in which displacement further occurs by a friction force and the restoration of displacement is limited by the elasticity of the tissue. Accordingly, the tissue can maintain a pressurized state in the state in which the insertion unit has been inserted, and the state in which displacement has occurred in the tissue surface and the target location can also be maintained.

As described above, although the insertion unit 10 is controlled to advance by the first length corresponding to the target location B, the insertion unit is not inserted by the first length within the tissue and thus does not reach the target location B (in this case, the insertion depth of the insertion unit may be D−a2). Accordingly, in order to compensate for this, in the present embodiment, the sensing unit 40 measures displacement of the tissue surface. The controller 50 may additionally control the operation of the insertion unit based on the measured displacement so that the end of the insertion unit 10 reaches the target location.

Figure 2D:
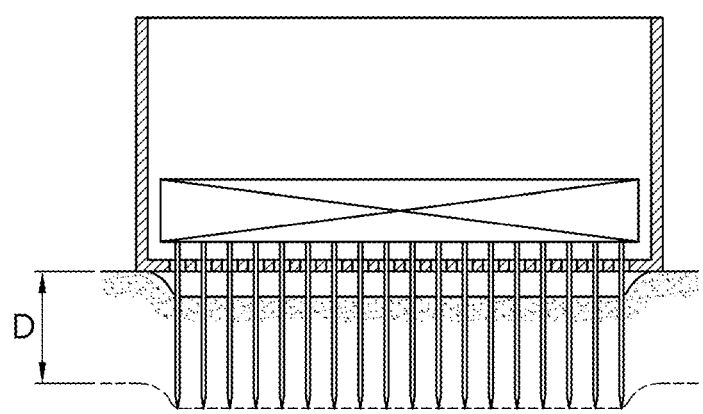

FIG. 2d is the state in which the insertion unit has been additionally inserted by a second length in FIG. 2c. In this case, the second length corresponds to a compensation depth by tissue displacement. By additionally inserting the insertion unit 10 by the second length as shown in FIG. 2d, the end of the insertion unit can reach the target location, and thus treatment may be performed.

Description is given based on FIG. 1. The sensing unit 40 is an element that measures displacement occurring in a surface of a tissue while the insertion unit is inserted. The sensing unit 40 may be configured using various sensor devices capable of measuring displacement.

For example, the sensing unit 40 may be configured using a photosensor positioned to neighbor a contact surface of the handpiece H coming into contact with the surface of the tissue. The photosensor may radiate light to the surface of the tissue and measure displacement of the surface by receiving light reflected by the surface. Alternatively, the sensing unit may be configured using an ultrasonic sensor positioned close to a contact surface of the handpiece. The ultrasonic sensor may sense ultrasonic waves generated by an emitter and reflected from a surface through a receiver, and may measure surface displacement of a tissue by analyzing the time lag, wavelength, etc. of the reflected ultrasonic waves. For another example, the sensing unit may include a movable member positioned to be movable in response to displacement of the tissue surface and a sensing unit and a sensing member measuring the amount of movement of the movable member. Specifically, the movable member is positioned to be supported by the surface of the tissue in the state in which it can freely move vertically. When the movable member moves by an amount corresponding to displacement occurred when tissue displacement occurs, the sensing member may measure displacement of the tissue surface by measuring the amount of movement of the movable member.

Meanwhile, the controller 50 may determine a value of the second length corresponding to a compensation depth based on displacement of a tissue surface measured by the sensing unit 40. In this case, the value of the second length may be a displacement value of a target location that is expected based on the displacement of the tissue surface. In this case, the characteristics of the tissue are different depending on a treatment portion, race, age, etc. The second length may be determined in various manners by taking into consideration the characteristics of the tissue.

For example, if a tissue corresponding to a treatment location has a low elasticity characteristic or if insertion has already been performed on a tissue in a pressurized state, displacement of a tissue surface and displacement within the tissue have almost a similar size. In this case, the controller 50 may determine a value of the second length to be the same as the displacement of the tissue surface.

In contrast, if a tissue has high elasticity, displacement of a tissue surface and displacement within the tissue may be different. For example, FIG. 3 is a graph showing the displacement characteristics of some tissues according to applied pressure. As shown in FIG. 3, in the state in which pressurization has been applied by the same force, relatively great displacement occurs on a tissue surface, whereas relatively small displacement occurs toward the inside of the tissue. In the case of a tissue having different displacement depending on the depth as described above, the controller 50 may determine a value of the second length through a separate calculation process using a displacement value of a measured surface as a variable or may determine a value of the second length with reference to the displacement value of the tissue surface and an already stored database.

When the value of the second length is determined as described above, the controller 50 compensates for an insufficient insertion depth by controlling the driving unit 20 so that the insertion unit 10 is additionally inserted by the second length. Accordingly, when the end of the insertion unit 10 reaches a target location, the controller 50 performs treatment at the target location by driving the treatment operation unit 30.

Figure 4:
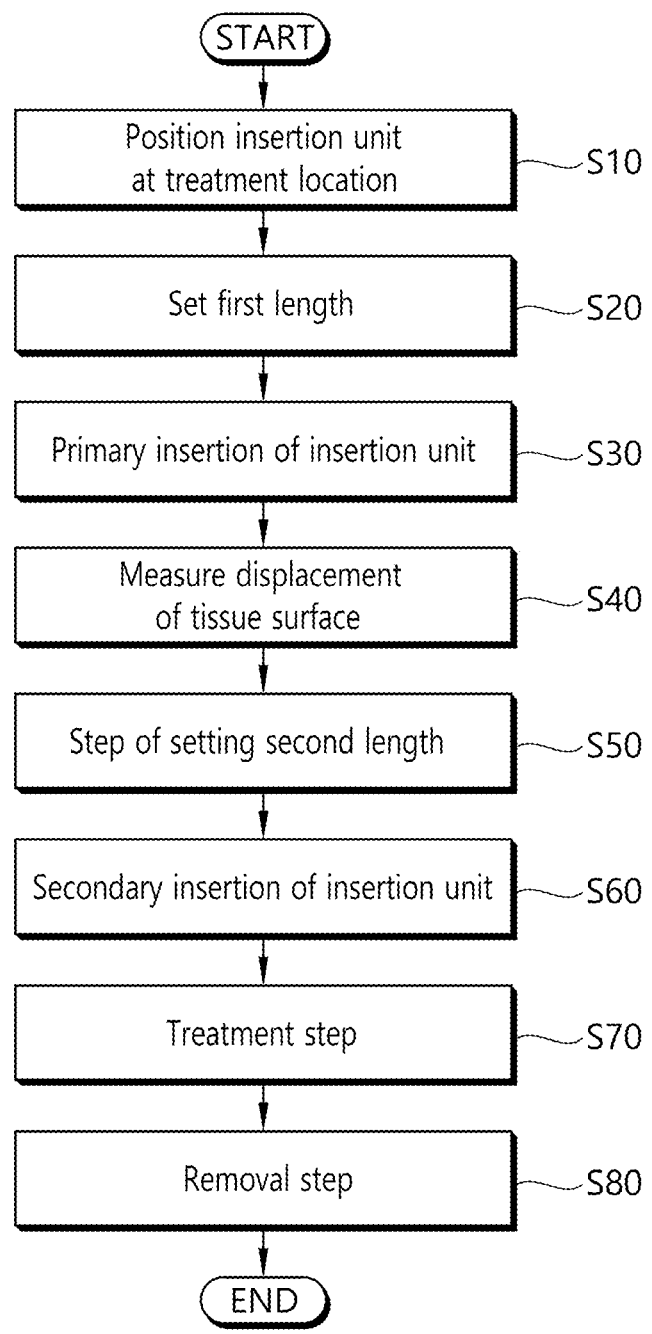
FIG. 4 is a flowchart showing a method of controlling the treatment apparatus of FIG. 1.

FIG. 4 is a flowchart showing a method of controlling the treatment apparatus of FIG. 1. Hereinafter, a method of controlling the treatment apparatus of the present embodiment is described with reference to FIG. 4.

First, the insertion unit 10 of the treatment apparatus is positioned at the treatment location of a tissue (S10). Specifically, one end of the handpiece to and from which the insertion unit 10 is advanced and retracted is positioned to neighbor or come into contact with a surface of the tissue corresponding to the treatment location.

Furthermore, the step of setting a first length is performed (S20). In this case, the first length is set to have a size corresponding to the depth of a target location B within the tissue. For example, the first length may be set as a distance value from the surface of the tissue that has not been pressurized to the target location. Or, the first length may be set as a distance value from a contact surface of the handpiece coming into contact with the surface of the tissue when treatment is performed to the target location. In this case, if the initial location of the insertion unit has been separated from the surface of the tissue, the first length may be a value of the sum of the distance from the initial location to the tissue surface and the target location from the tissue surface.

Thereafter, the step of primarily inserting the insertion unit is performed (S30). The controller 50 drives the driving unit 20 so that the insertion unit 10 is advanced by the first length and thus inserted into the tissue through the surface of the tissue. In this process, displacement of the tissue occurs as the tissue is pressurized, so the insertion unit 10 may not reach the target location.

Furthermore, the sensing unit 40 measures displacement occurred in the surface of the tissue while the primary insertion step is performed or right after the primary insertion step is performed (S40). In this case, the measured displacement may be displacement measured using a tissue surface right before the insertion unit pressurizes the tissue surface as a reference location. In this step, the insertion unit 10 may measure the displacement of the tissue surface in the state in which the primary insertion step has been completed. In this case, if it is determined that a difference between values is very small depending on characteristics of a tissue, for the consecutive execution of subsequent steps, a surface displacement value when the insertion unit penetrates the tissue surface or a surface displacement value while the primary insertion step is performed may be measured and used. The sensing unit 40 measures displacement using the aforementioned various sensing methods. The measured displacement value is transmitted to the controller 50.

The controller 50 sets a second length corresponding to a compensation depth based on the measured displacement value (S60). A value of the second length may be determined using various methods as described above. For example, the second length may be set as the same value as a displacement value of the tissue surface sensed by the sensing unit. Alternatively, the value of the second length may be obtained through a separate calculation process using a displacement value of the tissue surface as a variable or may be determined with reference to the displacement value of the tissue surface and a preset database.

When the second length is set, the controller 50 additionally controls the insertion operation of the insertion unit 10 based on the set second length (S60). This step is a secondary insertion step, and includes additionally inserting the insertion unit by the second length by driving the driving unit 20. Accordingly, the end of the insertion unit 10 may reach up to the target location.

When the end of the insertion unit 10 reaches the target location, the controller 50 performs a treatment step by driving the treatment operation unit 30 (S70). This step may be performed in various forms depending on a treatment method of the treatment apparatus. For example, a treatment substance from the treatment operation unit may be transferred and injected into the target location through the end of the insertion unit. Alternatively, the treatment operation unit may generate RF energy and deliver electrical energy to the target location through an electrode at the end of the insertion unit.

When the treatment is terminated through the aforementioned process, the controller 50 terminates the operation of the treatment operation unit 30 and performs the step of retracting the insertion unit 10 by controlling the driving unit 20 (S80). Through this step, the insertion unit 10 inserted into the tissue is drawn out from the tissue surface, so the treatment at the corresponding treatment location may be completed.

The steps of the method of controlling the treatment apparatus according to the present invention have been described above. The steps have been illustrated as being sequentially performed in FIG. 4, but the present invention is not limited thereto. The sequence of the steps may be changed and performed or the plurality of steps may be performed at the same time. For example, the step of setting the first length may be performed before the insertion unit is positioned at the treatment location. Furthermore, the primary insertion step and the step of measuring displacement may be performed at the same time, and displacement may be measured before the primary insertion step is completed. Furthermore, although the primary insertion step and the secondary insertion step have been illustrated as being separated steps, the two steps may be consecutively performed.

In accordance with the aforementioned embodiment, in performing invasive treatment, although a target location is moved due to the insertion of the insertion unit, treatment can be performed at an accurate location by compensating for an insertion depth.

Hereinafter, other embodiments in which the aforementioned embodiments have been further embodied are described. That is, in the following embodiments, the technical contents of the aforementioned embodiments have been applied to a treatment apparatus for the skin. The elements of the following embodiments corresponding to the elements of the aforementioned embodiments should be construed as being capable of implementing the technical contents of the aforementioned embodiments. In this case, in order to avoid redundant description in describing the present embodiment, a detailed description of contents corresponding to the aforementioned embodiments is omitted.

Figure 5:
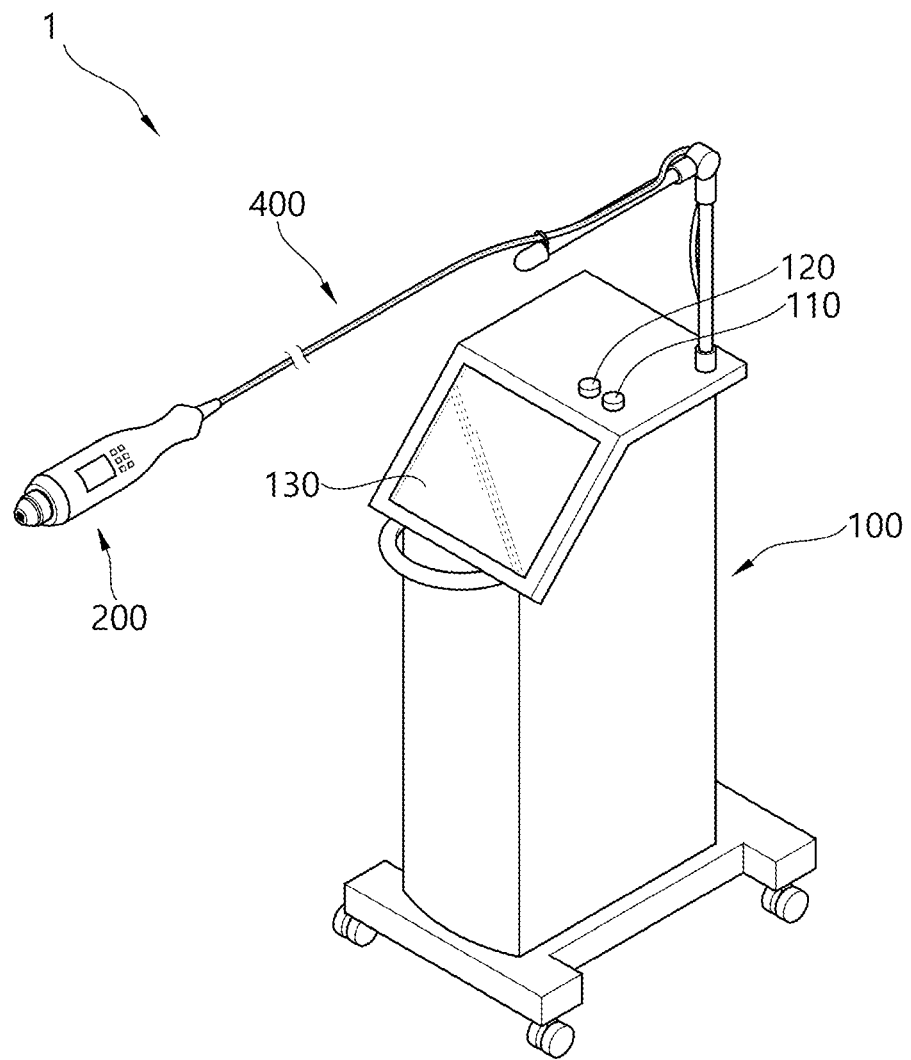
FIG. 5 is a perspective view showing a treatment apparatus according to another embodiment of the present invention.
Figure 6:
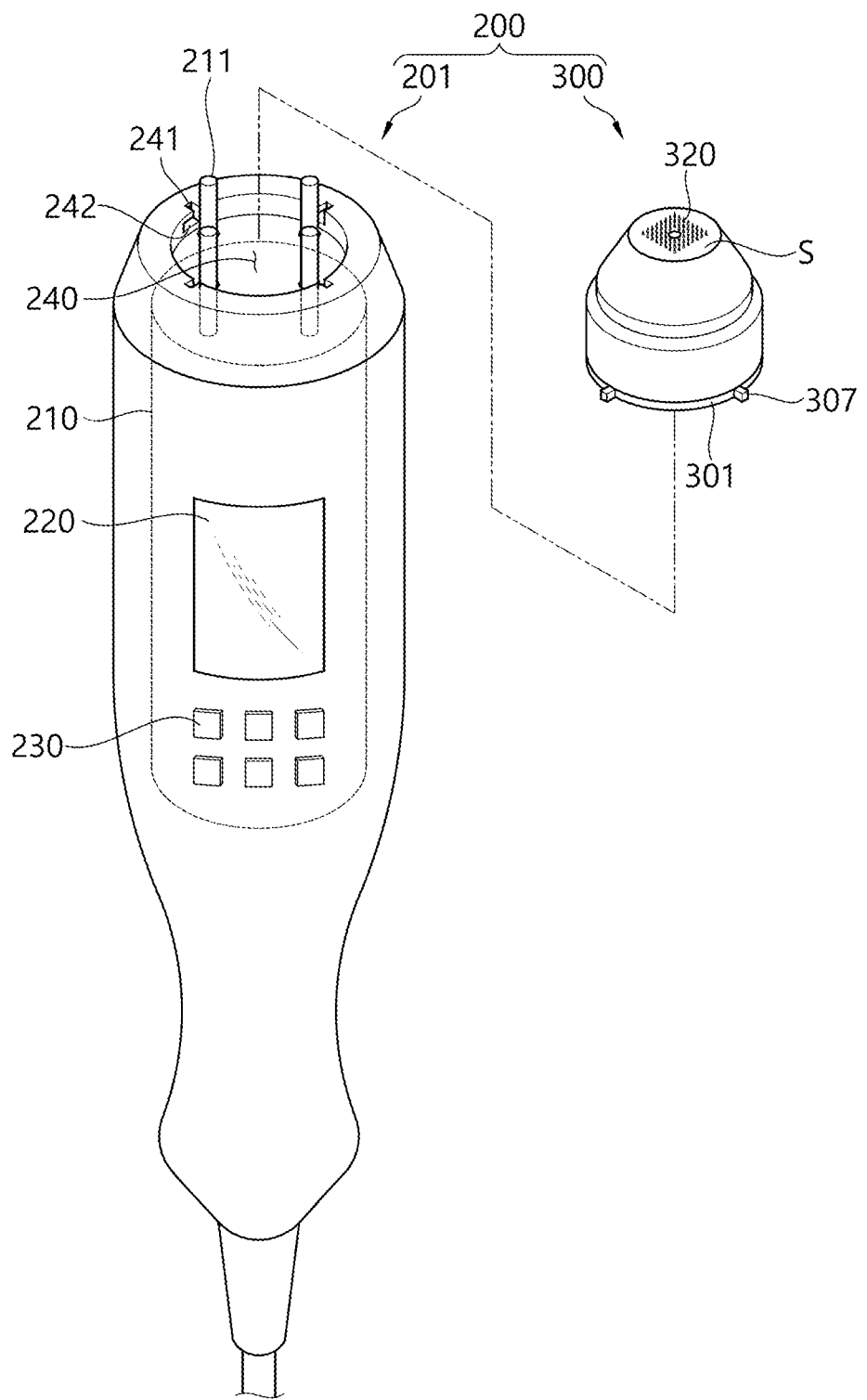
FIG. 6 is a perspective view showing the handpiece of the treatment apparatus of FIG. 5.

FIG. 5 is a perspective view showing a treatment apparatus according to another embodiment of the present invention. FIG. 6 is a perspective view showing the handpiece of the treatment apparatus of FIG. 5. The treatment apparatus 1 according to the present invention is an apparatus in which the insertion unit is inserted into a skin tissue of the human body and transfers energy to the inside of the skin tissue. The insertion unit of the present embodiment includes a plurality of needles, and may transfer energy to the inside of a skin tissue through the ends of the needles. Referring to FIGS. 5 and 6, the treatment apparatus according to the present invention includes a main body 100, a handpiece 200 that is graphed by a user and through which treatment can be performed, and a connection unit 400 connecting the main body and the handpiece.

An RF generator (not shown) may be provided within the main body 100. The RF generator is an element corresponding to the treatment operation unit (refer to 30 of FIG. 1) of the aforementioned embodiment, and generates RF energy used for treatment. The frequency of the RF energy generated by the RF generator may be controlled depending on the physical constitution, treatment purpose, a treatment portion, etc., of a patient. For example, RF energy used for skin treatment may be adjusted in the range of 0.1 to 0.8 MHz.

A power on/off switch 110, a frequency control lever 120 capable of controlling the frequency of RF energy generated by the RF generator, and a touch screen 130 displaying a variety of types of information including the operating contents of the treatment apparatus, enabling a user to input a command, and displaying treatment information may be positioned on an external surface of the main body 100.

Meanwhile, the handpiece 200 is connected to the main body by the connection unit 400. The connection unit 400 may transfer RF energy generated by the RF generator of the main body to a plurality of needles 320 corresponding to the insertion unit of the aforementioned embodiment, and may transfer power from the main body, which is necessary for various elements on the handpiece side to operate. The connection unit 400 is configured in a cable form, and may use a cable including a plurality of conducting wires whose metal lines are surrounded by insulating coating.

A driving unit 210 is positioned within the handpiece 200. The driving unit 210 is configured to linearly move output terminals 211 provided at the end of the driving unit in the length direction. When the output terminals 211 linearly move, the plurality of needles 320 disposed at the ends of the output terminals may pop in and out to the outside of the contact surface of the handpiece. Accordingly, the plurality of needles 320 may be inserted into a tissue of a patient or drawn out from the tissue by the driving of the driving unit 210. The driving unit 210 may be configured using a linear actuator using a solenoid, a hydraulic/pneumatic cylinder, etc.

A handpiece manipulation unit 230 and a handpiece display unit 220 may be provided on an external surface of the handpiece 200. The handpiece manipulation unit 230 is configured to manipulate the on/off of the handpiece, control the insertion depth of the insertion unit, or control the amount of energy transferred through the insertion unit. The handpiece display unit 220 may display a variety of types of information necessary in a set mode or during treatment with respect to a user. Accordingly, in the state in which the user has graphed the handpiece, the user can easily manipulate treatment contents during treatment through the handpiece manipulation unit 230, and can easily check treatment contents through the handpiece display unit 220.

A tip module 300 is provided at the end of the handpiece. The tip module includes the plurality of needles and may be detachably positioned at the main body 201 of the handpiece. Specifically, a base 301 forms the bottom of the tip module, and outward protruded detachment protrusions 307 are formed at the outer wall of the base. Guide grooves 241 that guides the detachment protrusions and an anti-separation groove 242 for preventing the detachment protrusions 307 guided along the guide grooves 241 from being separated are formed in a recess unit 240 to which the tip module is coupled on the handpiece side. Furthermore, the detachment protrusions 307 of the tip module are disposed at the handpiece in such manner that they are guided along the guide grooves 241 and coupled to the anti-separation groove 242. In this case, an example in which the tip module is detachably positioned at the handpiece as in the present embodiment is illustrative, and the tip module may be integrated with the handpiece.

Figure 7:
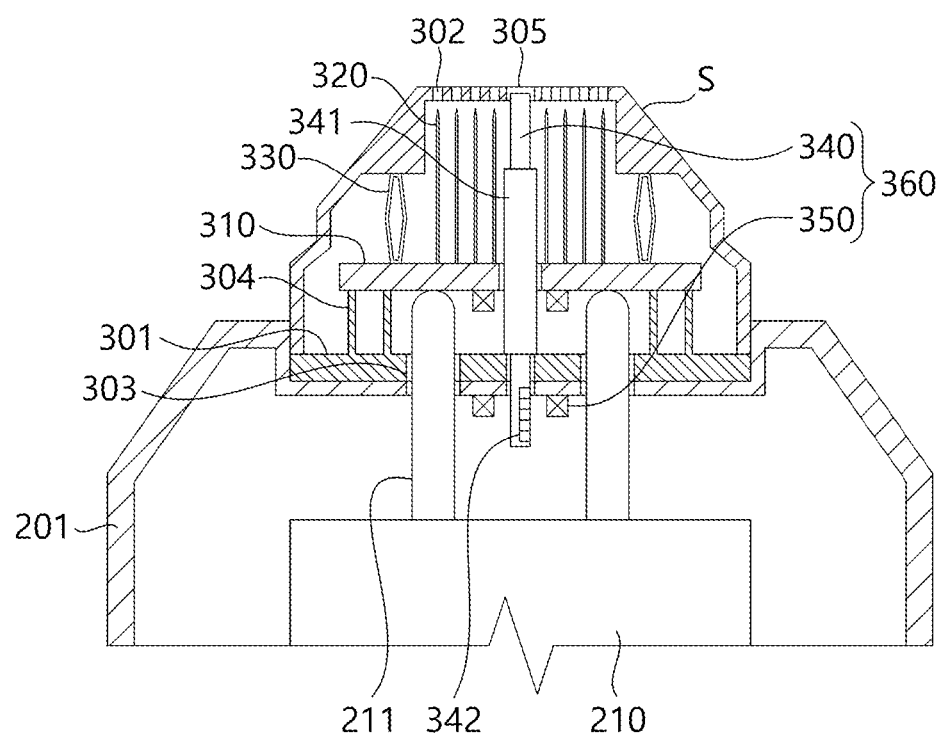
FIG. 7 is a cross-sectional view of the end of the handpiece of FIG. 6.

FIG. 7 is a cross-sectional view of the end of the handpiece of FIG. 6. Referring to FIG. 7, the end of the handpiece 200 is a portion that comes into contact with a skin tissue and where treatment is performed. A support plate 310 in which the plurality of needles 320 is disposed is provided within the tip module. The plurality of needles 320 is fixed and disposed in the support plate 310 in a matrix form. RF energy is transferred to the plurality of needles through a circuit formed in the support plate 310. The front S of the tip module may form a portion that neighbors or comes into contact with the skin of a patient upon treatment. A plurality of through holes 302 through which the plurality of needles pops in and out is formed in the front S.

At least one hole 303 through which the output terminal 211 can pass is provided at the bottom of the tip module. The output terminal 211 pressurizes the support plate 310 while linearly moving along the hole 303 when the driving unit 210 operates. The back of the support plate 310 is seated in a support 304 within the tip module. The front of the support plate 310 is pressurized by an elastic member 330 positioned within the tip module. When the output terminal 211 moves and pressurizes the support plate 310, the support plate 310 is separated from the support 304 and is advanced. Accordingly, the plurality of needles 320 pop out to the front of the through hole 302 and is inserted into a skin tissue. Furthermore, when the output terminal 211 is retracted by the driving of the driving unit 210, the support plate 310 is retracted by the restoring force of the elastic member 330, and thus the plurality of needles 320 also returns to the inside of the tip module. Although not separately shown in the drawing, a separate guide member for guiding the path along which the aforementioned support plate moves may be further provided.

Although not specifically shown in the drawing, the circuit of the support plate 310 may be configured to be electrically connected to the RF generator of the main body when the tip module is positioned in the handpiece. Alternatively, the circuit of the support plate may be selectively configured to be electrically connected to the RF generator when the support plate is pressurized by the output terminal 211 (e.g., an electrode may be formed at the end of the output terminal and may be electrically connected to the support plate upon pressurization).

Figure 8:
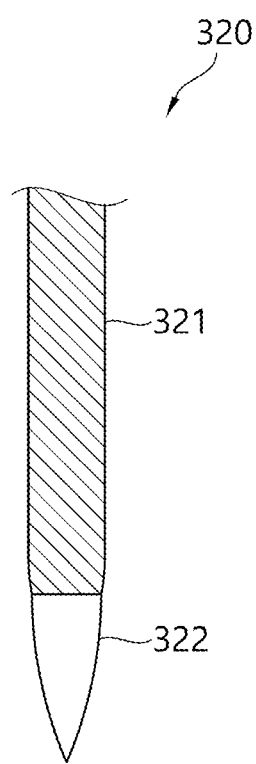
FIG. 8 is a cross-sectional view showing a cross section of one of a plurality of needles of FIG. 7.

FIG. 8 is a cross-sectional view showing a cross section of one of a plurality of needles of FIG. 7. Each needle 320 may be a micro needle having a diameter of approximately 5 to 500 μm. The needle 320 is made of a conductive material so that it can transfer RF energy. A portion that belongs to a surface of each needle and that excludes a tip thereof is made of an insulating material 321 so that RF energy is not transferred to a tissue. Accordingly, part of the tip of each needle functions as an electrode 322, and the needle is configured to transfer RF energy to a tissue through the tip. Accordingly, during treatment, the needle can selectively transfer RF energy to a portion where the end of the needle is positioned.

Referring back to FIG. 7, a sensing unit 360 is provided at the end of the handpiece 200. The sensing unit 360 measures displacement of a skin surface during treatment. For example, the sensing unit 360 includes a movable member 340 positioned to be movable in the insertion direction of the needles 320 and a sensing member 350 detecting the amount of movement of the movable member.

As shown in FIG. 7 the movable member 340 may be provided in the tip module. Movable member holes 305 are formed at both ends of the tip module, so the movable member 340 is positioned in a form to penetrate the tip module along the movable member holes 305. A stopper 341 having a greater diameter than the movable member hole may be formed in the body of the movable member 340. Accordingly, the movable member 340 can freely move without restriction in the vertical direction, that is, in the moving direction of the needles, within the range in which the movement of the movable member 340 is not restricted by the stopper 341. At this time, the front part of the movable member 340 coming into contact with a surface of a skin tissue during treatment may be configured to be exposed toward the front of the tip module in a maximum advancement state and to be received within the tip module in a maximum retraction state. Furthermore, the rear part of the movable member 340 may be configured to be protruded toward the back of the tip module in a maximum advancement state and maximum retracted state.

The sensing member 350 is configured to be positioned within the main body 100 of the handpiece separately from the tip module (refer to FIG. 7), and detects the amount of movement of the movable member 340. For example, the sensing member 350 is configured to detect a change in the magnetic field. Furthermore, the sensing member 350 may detect a change in the magnetic field according to a movement of a magnetic body 342 provided at the back of the movable member, and may measure the amount of movement of the movable member 340 based on the detected change.

Figure 9:
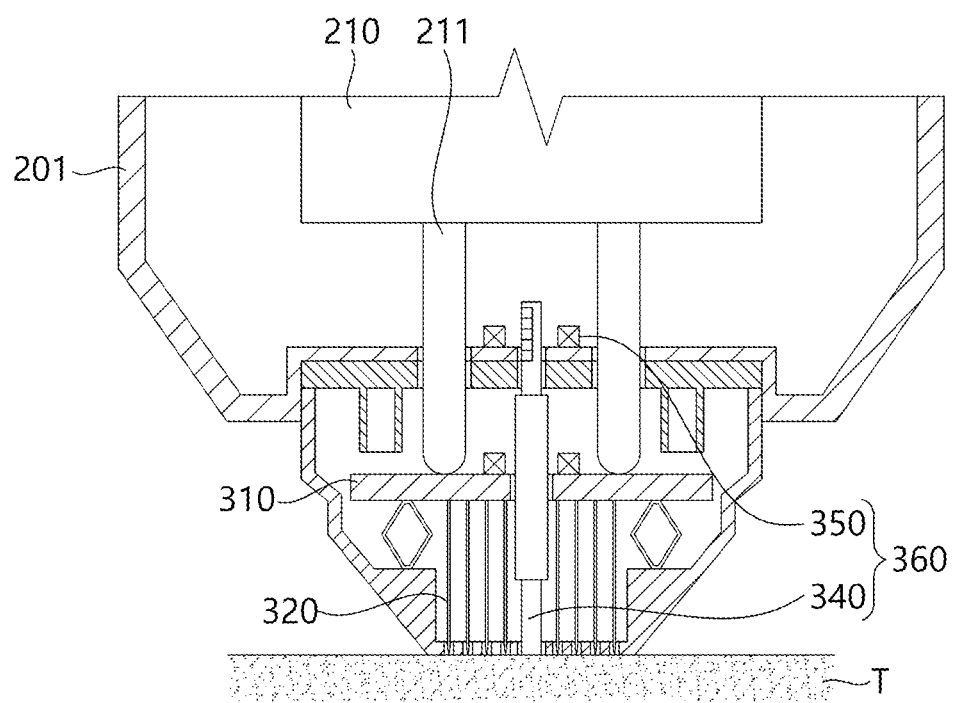
FIG. 9 is a cross-sectional view showing the state right before the needles are inserted during a treatment process using the handpiece of FIG. 7.
Figure 10:
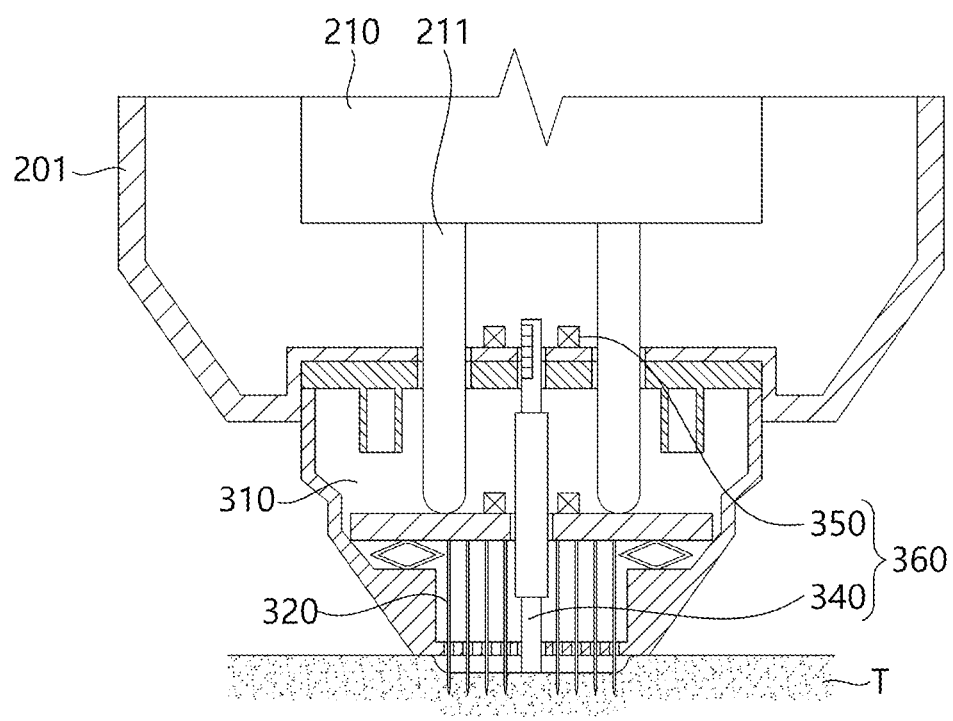
FIG. 10 is a cross-sectional view showing the state in which the needles have been inserted during a treatment process using the handpiece of FIG. 7.

FIG. 9 is a cross-sectional view showing the state right before the needles are inserted during a treatment process using the handpiece of FIG. 7. FIG. 10 is a cross-sectional view showing the state in which the needles have been inserted during a treatment process using the handpiece of FIG. 7.

As shown in FIG. 9, upon treatment, the end (the end equipped with the needles) of the handpiece is downward positioned to come into contact with a skin tissue T. In this case, the movable member 340 moves downward by gravity, comes into contact with the skin surface, and maintains the state in which it is supported by the skin surface. Furthermore, as shown in FIG. 10, when downward displacement occurs in the skin surface due to the insertion of the needles 320, the movable member 340 also moves downward by the displacement of the skin surface. At this time, the sensing member may measure the displacement of the skin surface by measuring the amount of movement of the movable member 340.

Figure 11:
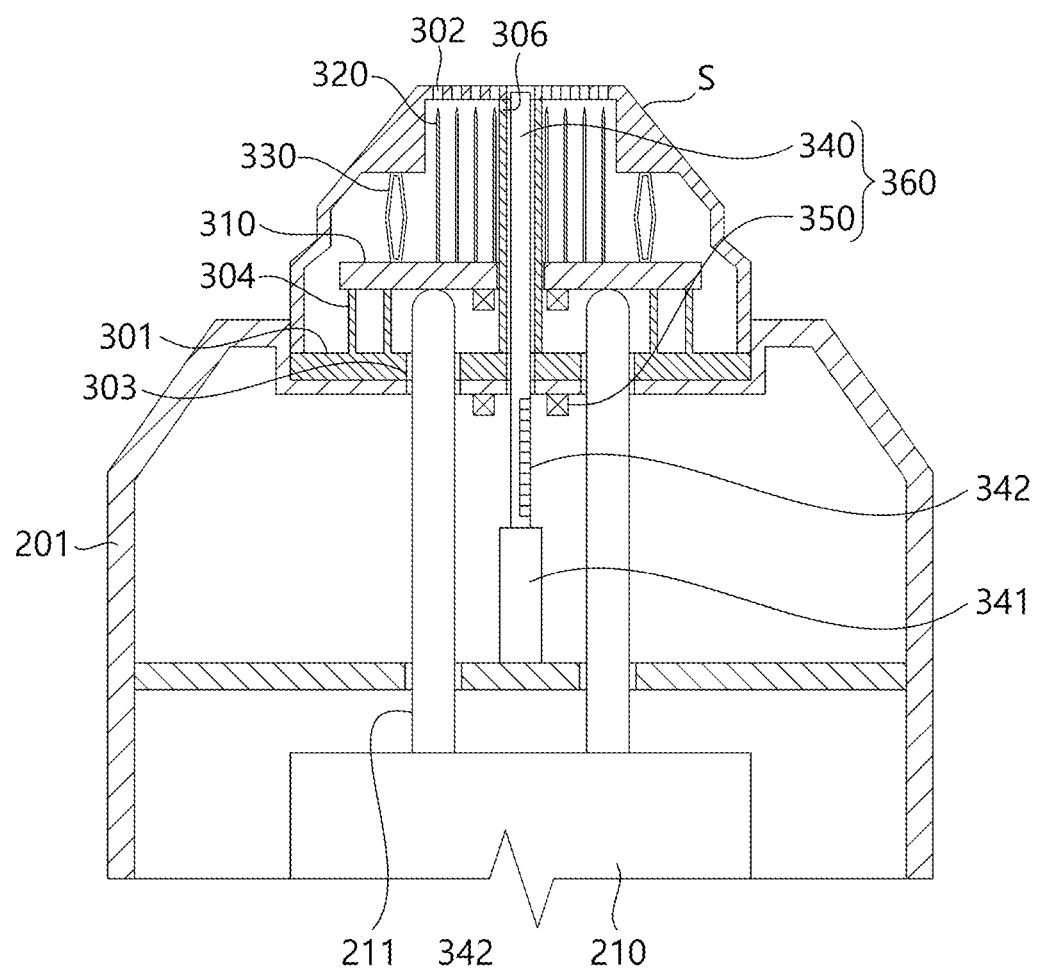
FIG. 11 is a cross-sectional view showing a modified embodiment of the handpiece of FIG. 6.

FIG. 11 is a cross-sectional view showing a modified embodiment of the handpiece of FIG. 6. In FIG. 7, the movable member of the sensing unit has been configured to be included in the tip module and the sensing member has been configured to be included in the main body of the handpiece. In contrast, as shown in FIG. 11, both the movable member and the sensing member may be configured to be included in the main body of the handpiece.

As shown in FIG. 11, a channel 306 through which the movable member can penetrate may be provided at the center of the tip module 300. Furthermore, the movable member 340 is positioned within the main body 201 of the handpiece to freely move in the insertion direction of the needles within the range in which the movable member 340 is not restricted by the stopper 341. At this time, the front part of the movable member 340 may be configured to be protruded and exposed toward the front of the tip module in a maximum advancement state, and may be configured to be received within the channel 306 of the tip module in a maximum retraction state. Furthermore, the sensing member 350 is positioned close to the back of the movable member 340, and may measure the amount of movement of the movable member 340 by sensing a change in the magnetic field by the magnetic body 342 positioned in the movable member.

As described above, FIGS. 7 and 11 show the configurations of various sensing units, but the sensing unit may be changed and implemented in other forms.

As in the aforementioned embodiment, the treatment apparatus of the present embodiment performs treatment in such a manner that the operations of the driving unit 210 and the RF generator (an element corresponding to the treatment operation unit of FIG. 3) are controlled and the plurality of needles 320 corresponding to the insertion unit (refer to 10 of FIG. 3) is inserted into a skin tissue and transfers RF energy to a target location based on the control. At this time, the controller determines the first length by taking into consideration the depth of the target location within the skin tissue, and determines the second length corresponding to a compensation depth according to displacement occurring when the needles are inserted. In this case, the sensing unit 360 may measure displacement of the skin surface occurring when the needles are inserted during treatment, and the controller (refer to 50 of FIG. 3) may determine the second length based on the measured displacement value. The controller performs a first insertion operation and a second insertion operation based on the determined first length and second length. Furthermore, when the ends of the needles reach the target location, the controller may perform treatment by driving the RF energy transfer unit so that RF energy is transferred to the target location. Accordingly, the RF energy is delivered to the dermal layer corresponding to the target location and heats the dermal layer, thereby being capable of causing the contraction of collagen to form a new collagen structure. Furthermore, when the treatment, is completed, the controller may drive the driving unit so that the plurality of needles is drawn out from the tissue, thereby being capable of terminating the treatment.

The steps of the method of controlling the treatment apparatus according to the present invention have been described above, and the detailed contents of the steps are substituted with the description of FIG. 4 of the aforementioned embodiment.

In this case, the step of setting the first length depending on a shape of the handpiece and an insertion method in the aforementioned step may be differently performed. Hereinafter, symbols are defined as follows for convenience of description.

L1: First length
Ld: Distance from a tissue surface to a target location in the normal state
Ld': Distance from the tissue surface to the target location in the pressurized state
L0: Distance that the end of the insertion unit has advanced from the initial location of the insertion unit until it reaches the tissue surface First, as shown in FIG. 2, if a tissue surface is not separately pressurized before the tissue surface is pressurized by the insertion unit, a value of the first length L1 may be set as a value of the Ld as described above.

In this case, if a contact surface of the handpiece and the end of the insertion unit are separated when the handpiece is positioned, the end of the insertion unit needs to advance by a given distance until it reaches the tissue surface. Accordingly, in this case, a value of the first length L1 may be set as a value of the sum of a value of the Ld and a value of the L0.

Moreover, a tissue surface has already been pressurized before the insertion unit pressurizes the tissue surface. For example, when the handpiece is positioned, the insertion unit may be inserted in the state in which a tissue surface has been pressurized through a contact surface of the handpiece. This state may be different from the state in which the distance from the tissue surface to a target location has not been pressurized depending on a characteristic of the tissue. Accordingly, in this case, a value of the first length L1 may be set as a value of the Ld' or may be set as a value of the sum of a value of the Ld' and a value of the L0. In this case, a value of the Ld' may be obtained using previously stored information of the database depending on the type of tissue.

Figure 12:
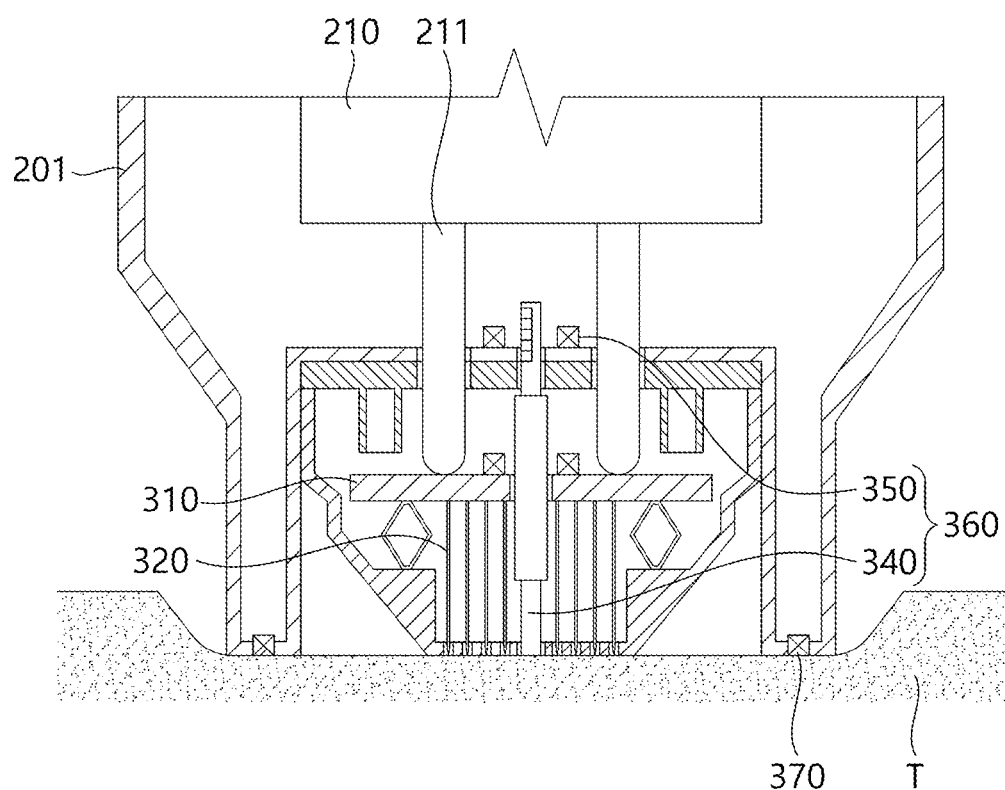
FIG. 12 is a cross-sectional view showing a cross section of the handpiece in an insertion operation according to another embodiment.

FIG. 12 is a cross-sectional view showing a cross section of the handpiece in an insertion operation according to another embodiment. FIG. 12 shows an element further including a pressure sensor at the end of the handpiece compared to the aforementioned embodiment. FIG. 12 shows a structure in which a contact surface is formed at the bottom of the case of the main body of the handpiece and the pressure sensor is positioned on the contact surface, but the end of a tip includes a contact surface and the pressure sensor is positioned at the end of the tip.

The pressure sensor may measure a force that a tissue surface is pressurized by a contact surface before the insertion operation of the insertion unit is performed. In this case, the controller may measure the amount of applied pressure through the pressure sensor and insert the insertion unit by controlling the driving unit when the applied pressure reaches a specific amount so that the insertion operation of the insertion unit is performed in the state in which tension of a given amount or more has been formed in the skin surface.

If the separate pressure sensor is provided in the contact surface as in the present embodiment, a value of the Ld' can be precisely checked in real time. A value of the Ld' can be accurately checked using measured information and information (e.g., the graph of FIG. 3) stored in the database because the applied pressure of a contact force can be measured in real time when treatment is performed. Accordingly, although applied pressure through a contact surface is greatly changed or a change in the distance up to a target location according to the applied pressure is great, treatment can be performed by accurately setting the first length value.

The treatment apparatus that performs treatment by transferring RF energy to a skin tissue has been chiefly described above. This is an example, and may be applied to a treatment apparatus aimed at another tissue not a skin tissue. Furthermore, the treatment apparatus may be applied to various treatment apparatuses, such as a treatment apparatus performing treatment using a method of transferring a treatment substance in addition to a treatment apparatus performing treatment using a method of transferring RF energy. Moreover, the treatment apparatus including the main body and the handpiece has been basically described, but is not limited thereto, and may be applied to a treatment apparatus configured in a single module form of the handpiece.

Although one embodiment of the present invention has been described in detail, the present invention is not limited to the embodiment. It is to be noted that a person having ordinary skill in the art to which the present invention pertains may modify or change the present invention in various manners without departing from the scope of the technical characteristics of the present invention defined in the claims.

The invention claimed is:

1. A treatment apparatus, comprising:
an insertion unit formed to be inserted into a tissue through a tissue surface, the insertion unit comprising a plurality of micro needles that selectively project from a contact surface of a handpiece, the handpiece contacting the tissue surface at the contact surface before the insertion unit is inserted into the tissue;
a displacement measurement unit measuring displacement of the tissue surface from the contact surface of the handpiece occurring due to an insertion of the insertion unit; and
a controller controlling an insertion operation of the insertion unit based on the displacement measured by the displacement measurement unit,
wherein the plurality of micro needles of the insertion unit are configured to move relative to the displacement measurement unit, and
wherein the displacement measurement unit comprises a movable member, and the movable member is provided to penetrate the contact surface of the handpiece and positioned to be movable in a progress direction of the insertion unit.

2. The treatment apparatus of claim 1, wherein the controller controls the insertion unit so that the insertion unit is additionally inserted as much as a size corresponding to the displacement occurred in the tissue surface so that an end of the insertion unit reaches up to a target location within the tissue.

3. The treatment apparatus of claim 1, wherein the controller controls the insertion unit based on a depth of a target location so that the insertion unit is advanced and inserted as much as a first length and controls the insertion unit so that the insertion unit is inserted as much as a second length in order to compensate for a depth into which the insertion unit has not been inserted due to the displacement of the tissue surface.

4. The treatment apparatus of claim 3, wherein the second length has a size identical with the displacement measured by the displacement measurement unit.

5. The treatment apparatus of claim 3, wherein the second length is calculated using a size of the displacement measured by the displacement measurement unit as a variable.

6. The treatment apparatus of claim 1, wherein the displacement measurement unit measures the displacement of the tissue surface before the insertion unit pressurizes the tissue surface and after the insertion unit is inserted through the tissue surface.

7. The treatment apparatus of claim 1, wherein the movable member moves as displacement occurs in the tissue surface, and
wherein the displacement measurement unit further comprises:
a sensing member measuring an amount of movement of the movable member.

8. The treatment apparatus of claim 7, wherein:
the movable member comprises a magnetic body, and
the sensing member senses the amount of movement of the movable member based on a change in a magnetic field generated when the movable member moves.

9. The treatment apparatus of claim 7, wherein:
the insertion unit is provided in a tip module detachably positioned in the handpiece or a main body, and
the movable member is provided to penetrate the tip module.

10. The treatment apparatus of claim 9, wherein the sensing member is disposed in the handpiece or the main body where the tip module is positioned.

11. The treatment apparatus of claim 1, wherein the insertion unit comprises an energy transfer member transferring energy to a target location in a state in which the insertion unit has been inserted into the tissue.

12. The treatment apparatus of claim 1, wherein the insertion unit comprises a substance transfer member transferring a treatment substance to a target location in a state in which the insertion unit has been inserted into the tissue.

13. A method of controlling a treatment apparatus, comprising steps of:
positioning an insertion unit on a tissue surface, wherein the insertion unit comprises a plurality of micro needles that selectively project from a contact surface of a handpiece;
inserting the insertion unit into a tissue through the tissue surface by pressurizing the insertion unit, the handpiece contacting the tissue surface at the contact surface before the insertion unit is inserted into the tissue;
measuring, by a displacement measurement unit, displacement of the tissue surface from the contact surface of the handpiece occurring due to the insertion of the insertion unit; and
controlling an insertion operation of the insertion unit based on the displacement,
wherein the plurality of micro needles of the insertion unit are configured to move relative to the displacement measurement unit, and
wherein the displacement measurement unit comprises a movable member, and the movable member is provided to penetrate the contact surface of the handpiece and positioned to be movable in a progress direction of the insertion unit.

14. The method of claim 13, wherein the step of controlling the insertion operation of the insertion unit comprises additionally inserting the insertion unit in order to compensate for a depth into which the insertion unit has not been inserted due to the displacement of the tissue surface.

15. The method of claim 14, further comprising a step of transferring a treatment substance into the tissue through the insertion unit.

16. The method of claim 13, wherein:
the step of inserting the insertion unit into the tissue comprises advancing and inserting the insertion unit as much as a first length based on a depth of a target location, and
the step of controlling the insertion operation of the insertion unit comprises additionally inserting the insertion unit as much as a second length based on a size of the displacement of the tissue surface.

17. The method of claim 13, wherein the step of controlling the insertion operation of the insertion unit comprises steps of:
calculating a compensation depth by taking into consideration the displacement of the tissue surface, and
additionally inserting the insertion unit as much as the calculated compensation depth.

18. The method of claim 13, wherein the step of measuring the displacement of the tissue surface comprises measuring the displacement of the tissue surface using the movable member that moves when the displacement of the tissue surface occurs and a sensing member measuring an amount of movement of the movable member.

19. The method of claim 18, wherein:
the movable member moves downward in a direction in which the displacement occurs when the displacement occurs in the tissue surface in the step of inserting the insertion unit, and
the sensing member measures the displacement by measuring the amount of movement of the movable member.

20. The method of claim 13, further comprising a step of transferring energy into the tissue through the insertion unit.

* * * * *